United States Patent [19]
Hueser

[11] 3,980,530
[45] Sept. 14, 1976

[54] TWO-ELECTRODE GAS ANALYSIS METHOD FOR ELECTRICALLY SENSING AND CONTROLLING REDOX REACTIONS

[76] Inventor: Rudolph L. Hueser, 1300 Fair Way, Space 23, Calistoga, Calif. 94515

[22] Filed: July 10, 1975

[21] Appl. No.: 594,714

Related U.S. Application Data
[62] Division of Ser. No. 398,006, Sept. 17, 1973, Pat. No. 3,912,613.

[52] U.S. Cl. ................................. 204/1 T; 204/1 R
[51] Int. Cl.² .......................................... G01N 27/46
[58] Field of Search ........ 204/1 T, 1 F, 1 M, 195 R, 204/195 T

[56] References Cited
UNITED STATES PATENTS

| | | | |
|---|---|---|---|
| 2,541,578 | 2/1951 | Egalon et al. | 204/195 R |
| 2,621,671 | 12/1952 | Eckfeldt | 204/1 M |
| 3,236,759 | 2/1966 | Robinson | 204/195 R |
| 3,314,864 | 4/1967 | Hersch | 204/195 R |
| 3,329,599 | 7/1967 | Brewer | 204/195 R |
| 3,713,994 | 1/1973 | Shults et al. | 204/1 F |

Primary Examiner—T. Tung
Attorney, Agent, or Firm—Christie, Parker & Hale

[57] ABSTRACT

A gas analysis system includes a pair of electrodes disposed in a cell containing an electrolyte through which a sample gas containing an unknown quantity of a reactant gas is passed. The gas reacts with the electrolyte, which changes the electrical resistance of the electrolyte in proportion to the concentration of the reactant gas. The electrodes are part of an externally-powered monitoring circuit which alternately senses the resistance of the electrolyte and then generates a voltage between the electrodes in response to the sensed resistance, permitting a generating current to flow periodically in response to the sensed resistance, the generating current being proportional to the amount of gas reacting with the electrolyte.

12 Claims, 5 Drawing Figures

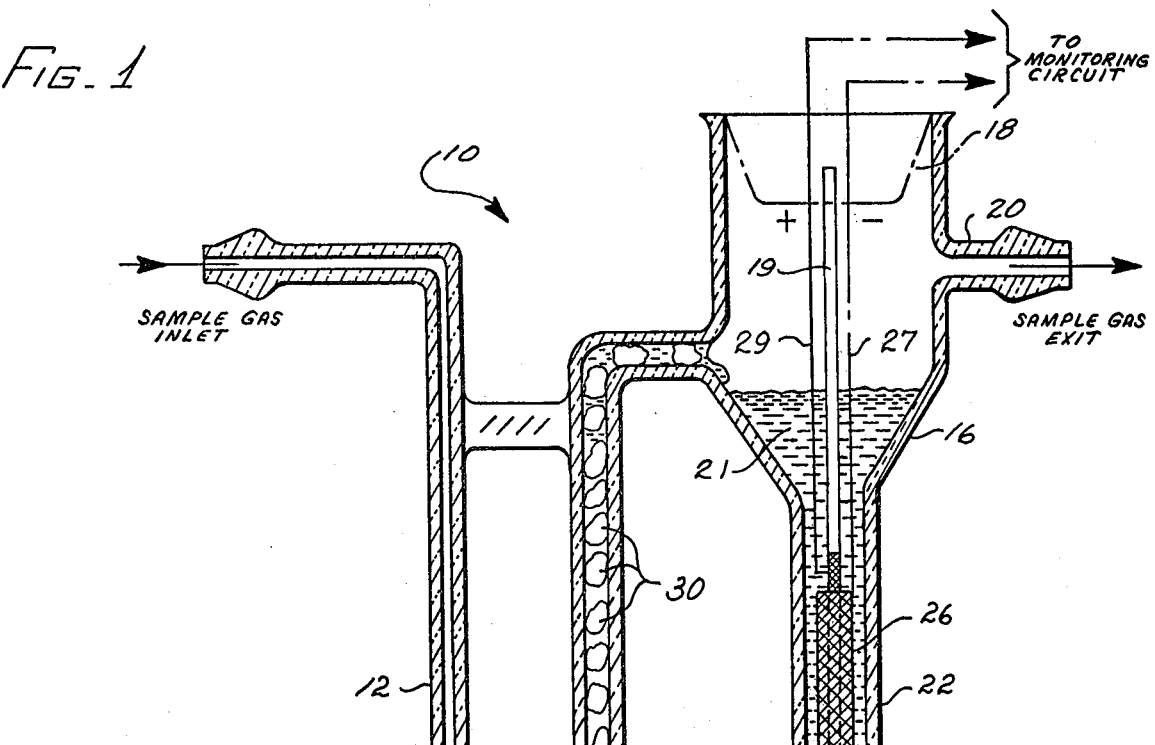
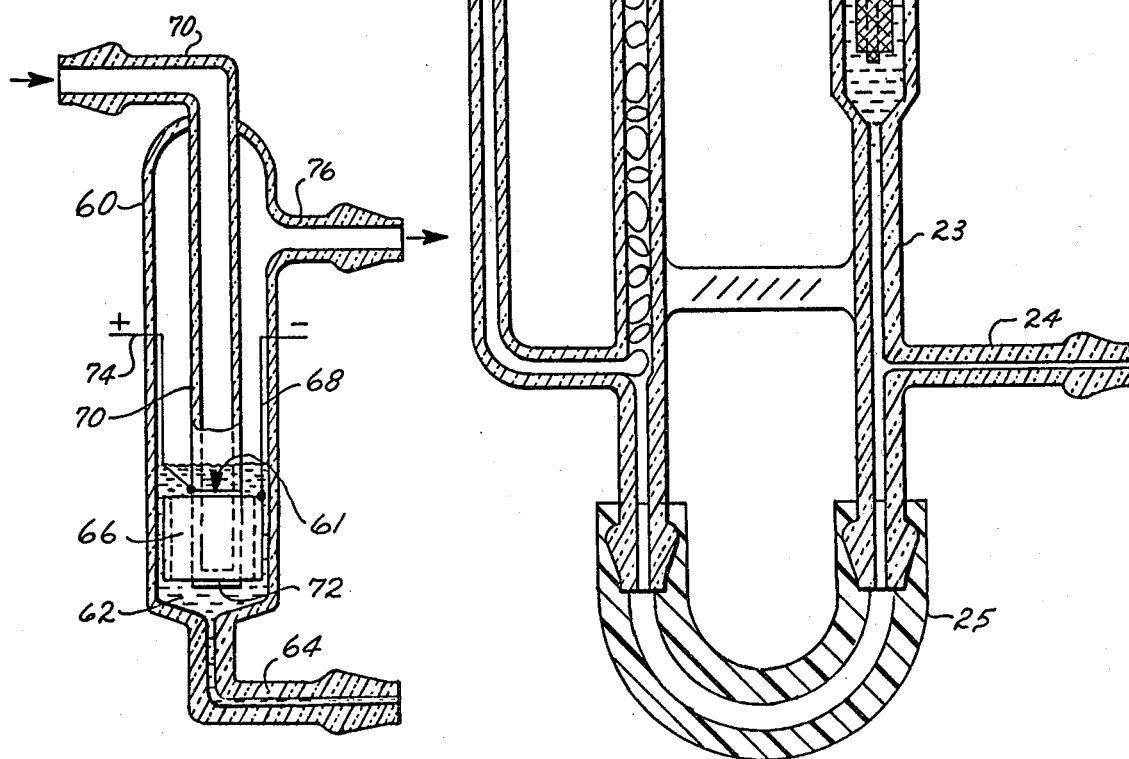

TWO-ELECTRODE GAS ANALYSIS METHOD FOR ELECTRICALLY SENSING AND CONTROLLING REDOX REACTIONS

This is a division of application Ser. No. 398,006, filed Sept. 17, 1973, now U.S. Pat. No. 3,912,613.

BACKGROUND OF THE INVENTION

This invention relates to gas analysis, and more particularly to an improved method and apparatus for determining the amount of a sample gas reacting with an electrolyte.

In the field of air pollution control it is necessary to measure the amount of pollutant in an exhaust gas stream. For example, it may be necessary to measure the quantity of noxious sulfides or sulfur dioxide in exhaust gases of factories or refineries.

A variety of ways are presently known by which the concentration of pollutant in a sample gas stream can be analyzed through redox reactions between the sample gas and an electrolyte. Generally speaking, the prior art electrolytic monitoring systems fall within two categories — those known as galvanic cells in which the electrical potential between the electrodes is provided by a self-contained source, and cells in which the potential between the electrodes is generated by an external power source.

The current flow between the electrodes in either a galvanic or an externally powered cell is proportional to the amount of reactant gas flowing in the system. In one commercial galvanic apparatus for measuring reducing reactant gases, an external electrical power supply generates free halogen at a predetermined rate, and the resulting signal level is monitored by a galvanic system. When a reactant gas is admitted to the apparatus, the decrease in signal level is a measure of the reactant concentration. Since galvanic systems are limited in the amount of electrical current they can produce, they are inadequate in analyzing sample gas streams containing high concentrations of reducing reactant gases.

In contrast, external power systems are not limited in their capacity to generate sufficient electrical energy to monitor the contents of sample gas streams containing a relatively large concentration of reactant gas. However, such monitoring systems in the past have been relatively complex because they have been comprised of three or more electrodes and elaborate hardware which make such systems relatively costly to produce and operate, together with being difficult to operate and being lacking in versatility.

SUMMARY OF THE INVENTION

This invention provides an externally-powered two-electrode system for electrically sensing and controlling redox reactions. The system is relatively simple in structure and inexpensive to produce and operate. The system also is capable of analyzing gas streams containing relatively large concentrations of reactant gas in addition to relatively small concentrations.

Briefly, the system includes a cell containing a body of electrolyte through which a sample gas stream to be analyzed is passed, and a pair of electrodes in the electrolyte. A monitoring circuit connected to the electrodes includes a sensing circuit for producing an output responsive to the electrical conductivity of the electrolyte present between the electrodes. A generating circuit responsive to the output of the sensing circuit produces either a sufficient generating voltage between the electrodes to electrolyze the electrolyte when the sensed conductivity of the electrolyte is within a first range, or it produces an insufficient voltage so the electrolyte will not be electrolyzed when the sensed conductivity is within a second range. The output voltage produced by the generating circuit produces a generating current which is proportional to the amount of gas reacting with the electrolyte. The output current is monitored to produce a continuous reading of the amount of reactant gas in the sample gas stream.

Preferably, the sensing circuit periodically measures the electrical resistance of the electrolyte/sample gas solution. The generating circuit responds to the resistance periodically measured by the sensing circuit to produce a periodic generating current which maintains a preset level of oxidant in solution by electrolysis of the electrolyte. The current flowing in the generating circuit is directly proportional to the quantity of gas reacted and is measured in the generating circuit in each period succeeding operation of the sensing circuit.

Thus, the voltages applied across the electrodes alternate between a first voltage pulse for measuring the amount of reacted gas in the system, and a second voltage pulse immediately following the first pulse for either producing generating current flow between the electrodes or not, depending upon the level of conductivity sensed by the first pulse.

These and other aspects of the invention will be more fully understood by referring to the following detailed description and the accompanying drawings.

BRIEF DESCRIPTION OF THE DRAWINGS

FIG. 1 is a schematic cross-sectional elevation view, partly broken away, showing an electrolytic cell used in the gas analysis system of this invention;

FIG. 5 is a schematic cross-sectional elevation view, partly broken away, showing an alternate embodiment of an electrolytic cell used in the gas analysis system of this invention.

DETAILED DESCRIPTION OF THE PREFERRED EMBODIMENTS

Figure 2:
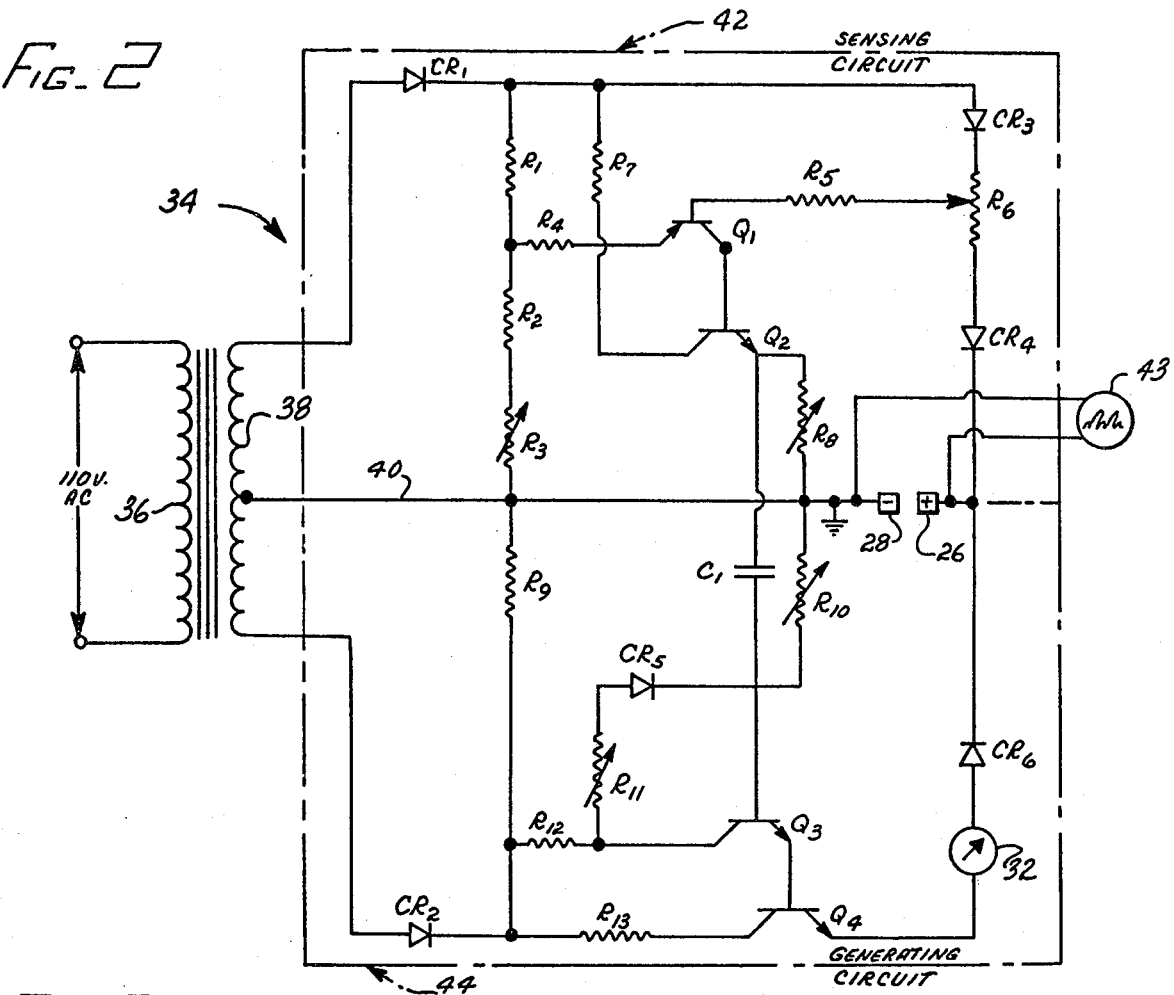
FIG. 2 is a schematic electrical diagram of the preferred monitoring circuit of this invention.

The present invention provides an externally-powered two-electrode system for electrically sensing and controlling redox reactions between a sample gas and an electrolyte. The system is useful in electro-chemically determining the exact quantities of those gaseous constituents of the sample gas which are oxidized to either a lower negative valence or a higher positive valence when they are allowed to react with a controlled quantity of an oxidant in an electrolyte. Several fields where this invention may be useful are in air pollution control both for emission control and air quality preservation, sewer gas control and monitoring, natural gas control and odorant monitoring, the protection of expensive platinum catalysts in petroleum refining, the control of stack emission and economizing of black liquor recovery in pulp and paper production, and the monitoring and control of both odorants and contaminants in the LPG industry.

One form of the present invention is described in the context of an electrolytic cell 10 shown schematically in FIG. 1. The cell is made from glass tubing and includes a small diameter tube 12 which serves as a sample gas inlet and which opens into the lower portion of an upright reaction tube 14. The top of the reaction tube opens into one side of a funnel-shaped gas separation chamber 16 of the cell. A sample gas exit tube 20 leads away from the opposite side of the separation chamber. A stopper shown in phantom line at 18 closes the top of the separation chamber. The bottom of the separation chamber tapers narrower downwardly and opens into an elongated upright medium-diameter tubular monitoring chamber 22 having an interior area wide enough to accommodate a pair of electrodes to be described in detail below. The electrodes are supported by a rod 19 made of non-conductive material. The medium-diameter section tapers narrower at its bottom and opens into a tubular section 23 of reduced diameter which is connected by a plastic tube 25 to the base of reaction tube 14 to provide a suitable means for allowing the electrolyte to return to the reaction tube. A small diameter tube 24 provides a connection to a reservoir (not shown) containing additional electrolyte so the liquid level in the cell is maintained within normal operating tolerances, and so the electrolyte is replenished as it is consumed.

The cell is filled with an electrolyte 21 comprised of an aqueous solution of a halide and free halogen, and in the following description the electrolyte will be considered to be aqueous hydrobromic acid containing a relatively high concentration of free bromine. A pair of electrodes are disposed in the electrolyte contained in tubular section 22. The electrodes preferably are both made of platinum, although other materials, including dissimilar elemental materials, may be used. In the use of dissimilar electrodes, for example, platinum and carbon may be effectively used. Preferably, both electrodes shown in FIG. 1 are made from platinum mesh screen rolled into two cylinders. The electrodes include a relatively large-diameter cylindrical screen 26 acting as the outer electrode. (A helix of platinum wire also has been used successfully as the outer electrode.) Screen 26 is connected to a conductor lead 27 of negative polarity so that screen 26 acts as the cathode of the monitoring circuit of this invention. A small-diameter cylindrical screen 28 is wound as tightly as possible around rod 19 and is disposed within the interior of screen 26. The small-diameter screen 28 is connected to a conductor lead 29 of positive polarity so the screen 28 provides the anode of the monitoring circuit of this invention. (The preferred polarity for this particular two-electrode cell configuration has not been proven.) The two electrodes are disposed one inside the other and in close proximity to each other. They are insulated from each other with plastic spacers (not shown) which do not appreciably impede the flow of electrolyte through the cell. The electrodes preferably are positioned below the junction of separation chamber 16 and monitoring chamber 22, and are located well below the surface of the electrolyte so the concentration of electrolyte contacting the electrodes during operation of the cell is an relatively homogeneous mixture.

During use of the cell the gas stream being monitored is forced through the sample gas inlet tube 12. The sample gas flow preferably is metered at a rate of about 150 ml per minute. The gas pressure at the sample gas inlet opening either may be slightly about atmospheric pressure, or the sample gas may be forced to flow through the cell by means of a reduced pressure applied to gas exit tube 20. As the sample gas leaves inlet tube 12 and enters the adjacent reaction tube 14, it mixes with the electrolyte in tube 14. For the purpose of the following explanation it will be assumed that the sample gas stream contains an amount of sulfur dioxide (reactant gas), the concentration of which is to be analyzed. As the sample gas enters the bottom of tube 14 the gas mixes with the electrolyte so that the sulfur dioxide reacts with free bromine at the liquid-gas interfaces and forms a train of bubles 30 which rise and transport the reacted electrolyte up in tube 14 and into the top portion of separation chamber 16. In the separation chamber the residual gas(es) and electrolyte separate, with the non-reacted portion of the sample gas flowing out exit tube 20. The electrolyte washes over the electrodes as it continuously circulates through the cell. The residual gas passing out through exit tube 20 will be devoid of any sulfur dioxide which has reacted with the free bromine in the electrolyte. Any sulfur dioxide present in the sample gas and which has reacted with the bromine reduces the bromine concentration of the electrolyte in monitoring chamber 22. Any change in the bromine concentration of the electrolyte present between the two electrodes will change the electrical resistance of the electrolyte between the electrodes in proportion to the change in the bromine concentration. Thus, an electrical generating current will start to flow between the electrodes in proportion to the change in bromine concentration to produce more elemental bromine by electrolysis. The bromine produced immediately goes into solution to replace the amount of bromine reacting with the sulfur dioxide. The current will be in direct proportion to the flow rate of the sulfur dioxide in the sample gas, and can be measured with a recorder or other suitable readout device, such as a meter 32 shown in FIG. 2.

FIG. 2 shows a preferred monitoring circuit 34 which is connected to the electrodes and is used to provide an output representing the concentration of reactant gas (sulfur dioxide, or other reducing gas) present in the sample gas. The monitoring circuit includes a transformer having an input winding 36 which receives power from an external 110 volt A.C. power supply. An output winding 38 of the transformer produces an output voltage of 12 volts A.C. A center tap 40 coupled to the output winding of the transformer applies the 12-volt A.C. signal evenly between a sensing circuit 42 and a generating circuit 44. A 6-volt potential from the transformer is applied to the sensing circuit through a diode $CR_1$ across a voltage divider which includes a resistor $R_1$ on one side of the divider and a resistor $R_2$ in series with a variable resistor $R_3$ on the other side of the divider. A current-limiting resistor $R_4$ is connected across the divider in series with the emitter of a P-N-P transistor $Q_1$ to be used to control operation of the generating circuit, as will be described in detail below. A biasing resistor $R_5$ is connected in series with the base of transistor $Q_1$ and also with the adjustable pick-off of a potentiometer $R_6$ connected in series between two diodes $CR_3$ and $CR_4$. Blocking diode $CR_4$ is also connected to anode 26, and diode $CR_3$, potentiometer $R_6$, diode $CR_4$ and the electrolyte comprise a second divider circuit in parallel with the first. The collector of transistor $Q_1$ is connected in series with the base of an N-P-N transistor $Q_2$, the collector of which is connected in series with a current-limiting resistor $R_7$. A variable resistor $R_8$ connected in series with the emitter of transistor $Q_2$ is connected to a common ground along with cathode 28 and the center tap 40 of the transformer.

Generating circuit 44 includes a resistor $R_9$ connected between the center tap of the transformer and a diode $CR_2$. A coupling capacitor $C_1$ is connected between the emitter of transistor $Q_2$ of the sensing circuit and the base of N-P-N transistor $Q_3$ of the generating circuit. A variable resistor $R_{10}$ is connected to the common ground and the base of $Q_3$. (Resistors $R_8$ and $R_{10}$ also are connected across capacitor $C_1$.) A variable biasing resistor $R_{11}$ and a blocking diode $CR_5$ are connected between the base and the collector of transistor $Q_3$, and a current-limiting resistor $R_{12}$ is connected between resistor $R_9$ and the collector of transistor $Q_3$. The emitter of transistor $Q_3$ is connected to the base of an N-P-N transistor $Q_4$ having a current-limiting resistor $R_{13}$ connected to its collector. The emitter of transistor $Q_4$ is connected in series with an electrical metering device 32, and a blocking diode $CR_6$ which is connected to anode 26.

In use, the monitoring circuit (including the electrolyte being present in the cell and containing a predetermined concentration level of free halogen suitable for the complete use of the particular component gas to be measured, and a sample gas stream containing no reactant gas flowing at an acceptable flow rate) is initially adjusted in the following manner: an oscilloscope 43 is connected across the electrodes, the oscilloscope being previously adjusted so that when an A.C. potential of the same frequency as the A.C. energy source, and having a peak-to-peak voltage of 2.0 volts, is connected to its signal input leads, two complete sine waves of a measurable magnitude are displayed on the face of the oscilloscope, and so that intervals of 2.0, 1.5, 1.0, and 0.5 volts may be readily ascertained and marked on the oscilloscope face with a suitable marker. With the oscilloscope so adjusted, the signal leads are transferred to the cell and connected to the electrodes as shown in FIG. 2. Resistor $R_3$ is preset at its minimum value, and resistors $R_8$, $R_{10}$ and $R_{11}$ are set at their maximum values. A D.C. milliammeter (not shown) is placed between the emitter to transistor $Q_2$ and ground. Potentiometer $R_6$ is now gradually adjusted from the minimum current set point until a sharp increase in current is noted on the milliammeter. At this point the adjustment is carefully continued until the current increase indicated slows perceptably. This is the optimum pickoff potential for potentiometer $R_6$, and the milliammeter may now be removed. The optimum resistance for potentiometer $R_6$ not only varies for each cell and electrode configuration, but also for each halogen concentration, and must be predetermined experimentally for each type of system. The selection of the proper resistance for potentiometer $R_6$ determines the voltage range of the sensing pulse for that particular system, and the resulting sensing pulse potential must be less than the electrolyzing potential of the electrolyte as indicated by oscilloscope 43. The sensing voltage between the two electrodes can vary, although the relatively low voltages (in the range of between 0.4 to 0.9 volt when hydrobromic acid is the halide) are preferred not only because this voltage level is below the level at which electrolysis of the electrolyte solution will occur, but also because in the lower voltage range the electrical conductivity of the electrolyte is entirely dependent upon the halogen concentration and not on the applied potential. The circuit adjustment may now be completed by gradually decreasing the resistance value of resistor $R_{11}$ and observing the oscilloscope. When the half-cycle sine wave associated with the generating circuit reaches the electrolyzing potential of the electrolyte, there will also be a sharp increase in generating current as noted by meter 32. Resistor $R_{11}$ is now readjusted so the generating pulse potential is just less than the electrolyzing potential. (In those cases where meter 32 still indicates current flow, this indicated value must be subtracted from the current indicated when a reactant gas is flowing to obtain a value which is truly proportional to the reactant flow rate. This is valid because the total halogen content of the electrolyte is neither increased nor decreased whenever the applied potential is less than the electrolyzing potential.) Resistors $R_3$, $R_8$, and $R_{10}$ normally remain at their present values, although they may be adjusted in some cases to refine the pickoff point of potentiometer $R_6$. When this condition has been obtained the circuit adjustments are completed and the oscilloscope may be removed.

The potentials at the emitter and base of transistor $Q_1$ are now in balance, with transistor $Q_1$ being in a conducting state, and its output amplified by transistor $Q_2$ which in turn charges capacitor $C_1$. The relatively low potential being applied across the electrodes is used to sense the bromine concentration of the electrolyte to determine whether or not additional bromine should be generated to replace any bromine which has reacted with the reactant gas in the sample gas stream. For example, if the sample gas stream contains a reactant gas, then the bromine level of the electrolyte will be reduced, which will increase the resistance present between electrodes 26 and 28, and thereby cause a generating current to flow between the electrodes. The magnitude of the current will be in direct proportion to the reactant gas flow rate, and can be measured by meter 32. On the other hand, if there is no reactant gas in the sample gas stream, then the bromine concentration of electrolyte solution will remain at a high level, and the low electrical resistance between the electrodes will result in the electrical voltage in the generating circuit being below 0.9 volt, which is below the electrolysis potential of the electrolyte, and will thereby prevent the generating circuit from producing more bromine.

Figure 3:
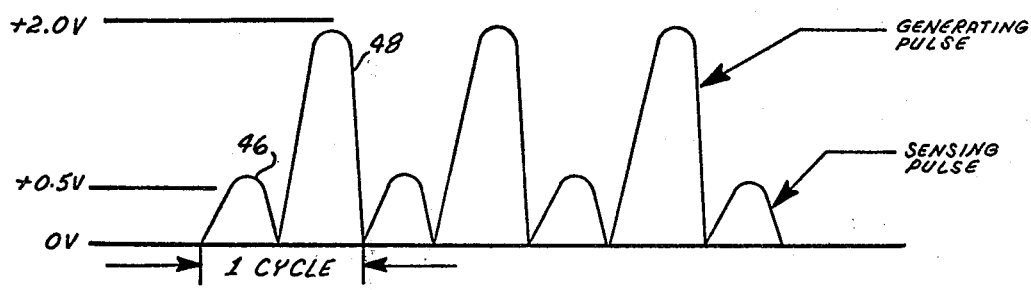
FIG. 3 is a graphical representation of typical electrode potentials occurring during operation of the monitoring circuit.

The typical functioning of the monitoring system is illustrated graphically in FIG. 3 which shows an alternating sensing pulse 46 produced by the sensing circuit in which the low, i.e., 0.6 volt, potential occurring between the electrodes senses whether or not the concentration of the oxidant in the electrolyte is sufficient to produce a generating pulse 48. If the concentration of the bromine is low (the electrolyte resistance higher than it was when the set point was established), then a generating pulse is produced during the generating portion of the operating cycle of the monitoring circuit. However, if the sensing pulse indicates that the concentration of bromine in the electrolyte is relatively high, (the resistance being equal to or less than when the set point was established) then any pulse produced will be at a lower potential than the electrolyzing potential.

Specifically with reference to the operation of the monitoring circuit shown in FIG. 2, assuming that the sample gas contains a reactant gas, the bromine concentration in the electrolyte solution drops, which results in an increased resistance between electrodes, the potential at the base of transistor $Q_1$ increases with respect to the potential at the emitter, causing transistor $Q_1$ to turn off. The charge normally maintained on coupling capacitor $C_1$ by the variable resistances $R_8$ and $R_{10}$ leaks off the capacitor when transistor $Q_1$ stops conducting and lowers the potential at the base of transistor $Q_3$. When the voltage at the base of transistor $Q_3$ is thus lowered relative to the potential at its emitter, transistor $Q_3$ begins conducting. The output of transistor $Q_3$ is amplified by transistor $Q_4$ to produce a relatively high voltage (over 1 volt when hydrobromic acid is the halide) across electrodes 26 and 28 which generates a current sufficient to maintain a present level of bromine in solution by means of electrolysis of the electrolyte so that the amount of bromine in the electrolyte being used up by the reactant gas in replaced. Thus, as described above, the amount of current required to replace the bromine being reacted is proportional to the flow rate of the reactant gas in the sample gas stream, so the reading provided on meter 32 of the generating pulses over a period of time will provide an indication of the concentration of reactant gas in the sample gas stream.

Conversely, if there is a relatively high bromine concentration of the electrolyte sensed during the sensing pulse of the monitoring circuit cycle, i.e. the sample gas ceases to contain a reactant gas, then the resistance between the electrodes decreases. This lowers the potential at the base of transistor $Q_1$ to a point lower than the potential across the the emitter of the transistor. Thus, transistor $Q_1$ begins conducting to charge capacitor $C_1$. The charge on the capacitor then raises the potential at the base of transistor $Q_3$ which will turn off transistor $Q_3$, and thereby prevent the generating circuit from producing a voltage between the electrodes sufficient to electrolyze the electrolyte. Thus, because the bromine concentration is relatively high, no further bromine generation is necessary.

Thus, the present invention provides an externally-powered two-electrode monitoring system which is relatively simple in construction and operation. Moreover, the system has sufficient capacity to monitor gas streams having high reactant concentrations because the capacity of the generating circuit is not limited as in the case of galvanic gas analysis systems.

Although the gas analysis system has been described in the context of analyzing sample gases containing reducing contaminant gases, oxidizing contaminant gases such as ozone can be measured without departing from the scope of this invention. For example, this may be accomplished by introducing a regulated quantity of reducing reactant gas, i.e., sulfur dioxide, into the cell to create an artificial "background" signal which then decreases in proportion to the amount of oxidant contaminant in the sample gas.

Figure 4:
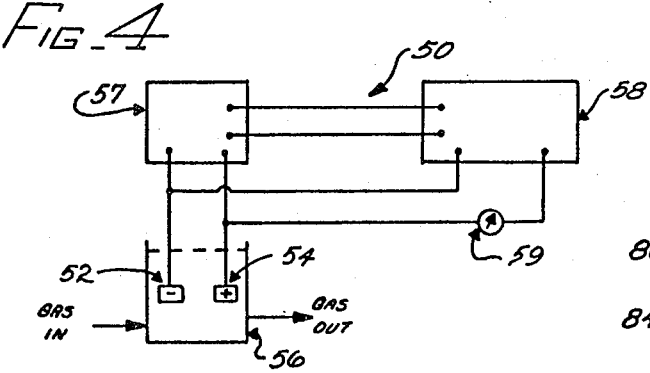
FIG. 4 is a schematic block diagram of an alternate monitoring circuit.

FIG. 4 shows an alternate monitoring circuit 50 in which the voltage potential for the sensing portion is provided by an EMF potential obtained by using electrodes 52 and 54 of dissimilar elemental materials, such as platinum and carbon, in an electrolyte solution contained in an electrolytic cell 56. Electrodes 52 and 54 are connected to the terminals of an electronic sensing circuit 57 (similar to sensing circuit 42 above) which controls an external power supply 58 to provide generating current to replenish the oxidant as it is consumed by the reactant gas. Sample gas containing a reactant gas is fed through the electrolyte solution in cell 56, and after the reactant gas reacts with the oxidant in the electrolyte, the remaining portion of the sample gas exits the cell. The amount of current flowing between the electrodes during the sensing period will be a function of the concentration of the oxidant in the electrolyte, and this current then will be used to trigger the power source 58 which either will or will not produce a generating current depending upon the amount of the current generated by the sensing circuit. Read-out meter 59 provides an indication of the amount of reactant gas contained in the sample gas stream.

FIG. 5 shows an alternate form of the cell provided by this invention in which a single upright reaction tube 60 contains a limited quantity of electrolyte 62 fed into the bottom of the cell through an inlet tube 64 from a reservoir (not shown). The minimal volume of active electrolyte in this type of cell accentuates its sensitivity to slight changes in reactant concentration, especially when the reactant concentration is in the low PPM concentration ranges. A cathode 66 submerged in the electrolyte comprises platinum foil shaped as an open-ended cylinder. A platinum lead wire 68 connected to the cathode cylinder 66 is adapted for suitable connection to a monitoring circuit in accordance with this invention. A glass frit 61 connected to the bottom of inlet tube 70 provides a sample gas inlet to the cell. Tub 70 extends downwardly through a major portion of the interior of the cell to a point immediately above the open top of the cathode cylinder. The fritted portion 61 of inlet tube 70 extends through the cylinder and mounts an anode made of platinum wire mesh screen 72 located concentrically inside cylindrical cathode 66. Alternatively, the anode may be provided by a vapor-deposited platinum coating on the surface of glass frit 61. A platinum lead wire 74 is connected to anode 72 and adapted for suitable connection to the monitoring circuit.

During use of the cell shown in FIG. 5, the open ends of the foil cathode not only provide a pathway for the unreacted sample gas to exit the immediate area of the electrodes upwardly, but they also cause the electrolyte between the electrodes to continually flow upwardly between the electrodes and downwardly outside the cathode. This action prevents electrode "polarization", and promotes a fast and sensitive response of the electrical circuits to slight changes in bromine concentration, whenever the sample gas contains a reactant gas component. Moreover, the location of the cathode and the anode in the immediate area where the reaction between the reactant gas and the oxidant takes place provides an extremely accurate way of measuring the instantaneous concentration of oxidant in solution, and thereby provides a highly accurate measurement of the reactant gas in the sample gas stream. Any portion of the sample gas stream which is not reacted passes out of the cell through a gas exit tube 76.

Figure 6:
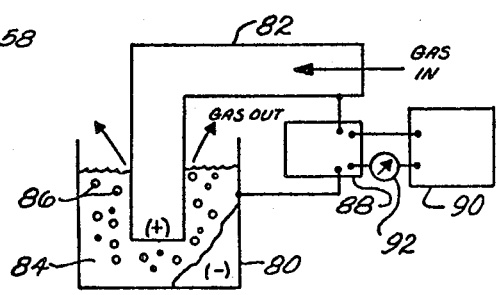
FIG. 6 is a schematic block diagram of a further alternate monitoring circuit.

FIG. 6 shows a further alternate form of the invention in which a container 80 of elemental material, such as platinum or carbon, acts as the cathode for the monitoring circuit. A sample gas inlet tube 82 of similar or dissimilar elemental material acts as the anode. An electrolyte 84 containing dissolved free halogen and halide in aqueous solution is disposed in the container with the bottom of the sample gas inlet tube 82 being submerged in the electrolyte. A sample gas containing reactant passes through the sample gas inlet tube and forms bubbles 86 to provide electrolyte circulation. A sensing and generating circuit 88 similar in configuration to the circuit shown in FIG. 2 is connected by suitable conductor leads to container 80 and inlet tube 82. The sensing and generating circuit is powered by an external power supply 90, and a read-out device 92 provides an indication of the amount of reactant gas contained in the sample gas stream.

I claim:

1. In a method of determining the amount of a reactant gas in a sample gas stream that will reduce the concentration of halogen, the steps of passing the sample gas stream through a body of aqueous halide electrolyte contained in a cell so the amount of reactant gas contained in the sample gas will react with free halogen dissolved in the electrolyte and reduce its electrical conductivity in an amount proportional to the amount of reactant gas in the sample gas stream, disposing a cathode and an anode in spaced apart relation in the aqueous electrolyte in the cell, producing a first voltage pulse between the cathode and the anode by a sensing circuit to monitor the electrical resistance of the electrolyte present between the cathode and the anode, and producing a second voltage pulse between the cathode and the anode, immediately following said first voltage pulse, by a generating circuit which is either sufficient to electrolyze the halide and form free halogen if the monitored electrical resistance of the electrolyte is within a first range or is insufficient to electrolyze the halide if the monitored electrical resistance of the electrolyte is within a second range.

2. The method according to claim 1 in which the electrolyte has a characteristic voltage level above which it can be electrolyzed and below which no electrolysis takes place, and in which the generating circuit produces a voltage pulse above said characteristic level if the monitored resistance is above a certain level, or in which the generating circuit produces a voltage pulse below said characteristic level if the monitored resistance is below the certain level.

3. The method according to claim 2 including periodically sensing via the sensing circuit the electrical resistance between the cathode and the anode, and periodically operating the generating circuit in response to the resistance monitored by the sensing circuit in the period immediately preceding each operative period of the generating circuit to produce a periodic output which is a function of the resistance periodically measured by the sensing circuit.

4. The method according to claim 3 including operating the sensing circuit and the generating circuit on power from an electrical power supply external to the cell and the electrolyte.

5. The method according to claim 4 including producing a first output signal via the sensing circuit when the electrical resistance of the electrolyte present between the cathode and the anode is above a certain level or producing a second output signal when the electrical resistance of the electrolyte present between the cathode and the anode is below the certain level, and activating the generating circuit in response either to the first output signal to apply a voltage pulse between the cathode and the anode sufficient to electrolyze the electrolyte or to the second output signal to apply a voltage pulse between the cathode and the anode insufficient to electrolyze the electrolyte.

6. The method according to claim 1 including recording the generating circuit current as an indication of the amount of the reactant in the sample gas stream.

7. The method according to claim 1 in which the portion of the cell contacting the electrolyte is made from an inert material.

8. The method according to claim 7 in which the cathode and anode are each made from an inert conductive material; and including disposing the cathode and anode within the cell so that each is submerged in the electrolyte and in free communication with each other through the electrolyte so that any change in free halogen concentration of the electrolyte can be sensed between the electrodes.

9. The method according to claim 1 in which the sensing and generating steps of the sensing and generating circuits, respectively, are alternately shared only by the cathode and the anode.

10. A method according to claim 1 including operating the sensing circuit and the generating circuit on power from an electrical power supply external to the cell and the electrolyte.

11. The method according to claim 1 including submerging the cathode and anode in said electrolyte, and reacting the sample gas stream with the electrolyte in the presence of the cathode and the anode.

12. The method according to claim 11 in which either of the cathode or anode is a cylindrical open-ended body, and the other is located in the interior of the cylinder; and including admitting the sample gas stream to the electrolyte at a location to provide circulation of the electrolyte through the cylinder.

* * * * *

UNITED STATES PATENT AND TRADEMARK OFFICE
CERTIFICATE OF CORRECTION

PATENT NO. : 3,980,530
DATED : September 14, 1976
INVENTOR(S) : RUDOLPH L. HEUSER It is certified that error appears in the above-identified patent and that said Letters Patent are hereby corrected as shown below:

[76] Inventor: "Hueser" should be -- Heuser --.

Col. 3, line 67, "an" should be -- a --.

Col. 4, line 5, "about" should be -- above --;

line 17, "bubles" should be -- bubbles --.

Col. 5, line 49, "to" should be -- of --.

Col. 6, line 23, "present" should be -- preset --.

Col. 7, line 18, "present" should be -- preset --;

line 21, "in" should be -- is --;

line 35, "across the the emitter" should be -- across the emitter --.

Col. 8, line 30, "Tub" should be -- Tube --.

Signed and Sealed this

Eighth Day of February 1977

[SEAL]

Attest:

RUTH C. MASON
*Attesting Officer*

C. MARSHALL DANN
*Commissioner of Patents and Trademarks*